United States Patent
Shin

(10) Patent No.: US 9,782,275 B2
(45) Date of Patent: Oct. 10, 2017

(54) METHOD AND SYSTEM FOR CONTROLLING WALKING OF WEARABLE BOOT

(71) Applicant: HYUNDAI MOTOR COMPANY, Seoul (KR)

(72) Inventor: Wan Jae Shin, Seoul (KR)

(73) Assignee: HYUNDAI MOTOR COMPANY, Seoul (KR)

(*) Notice: Subject to any disclaimer, the term of this patent is extended or adjusted under 35 U.S.C. 154(b) by 51 days.

(21) Appl. No.: 14/931,607

(22) Filed: Nov. 3, 2015

(65) Prior Publication Data

US 2017/0007426 A1    Jan. 12, 2017

(30) Foreign Application Priority Data

Jul. 6, 2015   (KR) .................. 10-2015-0095864

(51) Int. Cl.
*G06F 19/00*   (2011.01)
*A61F 2/60*   (2006.01)
(Continued)

(52) U.S. Cl.
CPC .............. *A61F 2/60* (2013.01); *A61F 5/0118* (2013.01); *B25J 9/0006* (2013.01); *Y10S 901/01* (2013.01)

(58) Field of Classification Search
CPC .. Y10S 901/01; Y10S 901/48; Y10S 482/901; B25J 9/0006; B25J 9/1664;
(Continued)

(56) References Cited

U.S. PATENT DOCUMENTS 6,484,068 B1 * 11/2002 Yamamoto ........... B25J 19/0016
                                                        198/380
6,845,830 B2 *  1/2005 Tojo ..................... A61G 5/046
                                                        180/8.3
(Continued)

FOREIGN PATENT DOCUMENTS

JP        09-131679        5/1997
JP        2008-73830       4/2008
(Continued)

OTHER PUBLICATIONS

A virtual force approach for cooperative standoff target tracking using multiple robots; Xun Wang; Daibing Zhang; Lincheng Shen; Jianwei Zhang; 2016 Chinese Control and Decision Conference (CCDC); Year: 2016; pp. 1348-1353, DOI: 10.1109/CCDC.2016. 7531194.*

(Continued)

*Primary Examiner* — Khoi Tran
*Assistant Examiner* — Jorge Peche
(74) *Attorney, Agent, or Firm* — Brinks Gilson & Lione

(57) ABSTRACT

Disclosed are systems and methods for controlling walking of a wearable robot, which provide walking assistive power as if something were pulling the wearer of the robot from the front or pushing the wearer from the back, by applying the force of a virtual spring, whereby the wearer may comfortably walk. The systems for controlling walking of the robot include: a walking mode determination unit configured to determine whether the robot is walking; a virtual spring force calculation unit configured to calculate the force of a virtual spring of which one end is connected to the robot and the other end is connected to a target point in front of the robot based on the walking direction; and a joint driving unit configured to drive each joint of the robot using torque (Continued)

calculated based on the force of the virtual spring, which is calculated by the virtual spring force calculation unit.

12 Claims, 4 Drawing Sheets

(51) Int. Cl.
  *B25J 9/00* (2006.01)
  *A61F 5/01* (2006.01)
(58) Field of Classification Search
  CPC . B25J 9/00; B25J 13/085; B25J 13/088; B25J 19/02; A61H 2201/5069; A61H 3/00; A61H 1/0237; A61H 1/0262; A61H 1/0244; A61H 2201/1261; A61H 2201/1642; A61H 2201/165; A61H 2201/5007; A61H 2205/10; A61H 2230/62; A61H 3/008; Y10T 74/20305; A61B 5/1124; A61B 2220/30; A61B 2220/40; A61B 2220/54; A61B 2220/803; A61F 2/60; A61F 2002/701; A61F 5/0102; G05B 2219/36036; G05B 2219/40519; A63B 21/00181
  See application file for complete search history.

(56) References Cited

U.S. PATENT DOCUMENTS

| | | | |
|---|---|---|---|
| 8,287,473 B2 * | 10/2012 | Yasuhara | A61F 5/0102 600/587 |
| 9,043,029 B2 * | 5/2015 | Seo | B25J 9/104 700/245 |
| 2007/0010913 A1 * | 1/2007 | Miyamoto | B25J 9/1658 700/264 |
| 2008/0147281 A1 * | 6/2008 | Ishii | B62D 51/005 701/49 |
| 2009/0227424 A1 * | 9/2009 | Hirata | A61B 5/1038 482/7 |
| 2010/0243344 A1 * | 9/2010 | Wyrobek | B25J 5/007 180/21 |
| 2011/0040216 A1 | 2/2011 | Herr et al. | |
| 2012/0310412 A1 * | 12/2012 | Seo | B25J 9/0006 700/254 |

FOREIGN PATENT DOCUMENTS

| | | |
|---|---|---|
| JP | 2012-143449 | 8/2012 |
| KR | 10-1179159 | 9/2012 |
| KR | 10-1321791 | 7/2013 |
| KR | 10-1315199 | 10/2013 |
| KR | 101438970 B1 | 9/2014 |

OTHER PUBLICATIONS

ScarlETH: Design and control of a planar running robot; Marco Hutter; C. David Remy; Mark A. Hoepflinger; Roland Siegwart; 2011 IEEE/RSJ International Conference on Intelligent Robots and Systems ; Year: 2011; pp. 562-567, DOI: 10.1109/IROS.2011.6094504.*

Online nonlinear reference shaping with end-point position feedback for human-like smooth reaching motion; Fumi Seto; Tomomichi Sugihara; 2009 9th IEEE-RAS International Conference on Humanoid Robots; Year: 2009; pp. 297-302, DOI: 10.1109/ICHR.2009.5379562.*

* cited by examiner

METHOD AND SYSTEM FOR CONTROLLING WALKING OF WEARABLE BOOT

CROSS REFERENCE TO RELATED APPLICATION

The present application claims priority to Korean Patent Application No. 10-2015-0095864, filed Jul. 6, 2015, the entire contents of which is incorporated herein by this reference.

BACKGROUND

Field of the Invention

The present disclosure relates to methods and systems for controlling walking of a wearable robot. More particularly, the present disclosure relates to methods and systems for controlling walking of a wearable robot, which may make a robot wearer's walking comfortable by providing force of a virtual spring as walking assistive power.

Description of the Related Art

Generally, a wearable robot is a device for helping a patient who has difficulty in walking or cannot walk unassisted to walk with the assistance of the robot while wearing the robot.

Algorithms developed thus far for assisting walking of a wearable robot may be largely categorized into a method in which previously input walking patterns are realized according to modes for patients who cannot move by themselves, and a method in which the force of the joint to move is measured and augmented for patients who can move by themselves but have weak muscular strength.

In the case of a wearable robot for assisting walking, research has been progressing in order that the wearer of the robot may walk in a way very similar to human walking and not feel resistance when wearing the robot.

Particularly, technology for reducing loads attributable to the weight of the robot to enable the wearer of a robot to comfortably walk has become a very important issue in related art.

The foregoing is intended merely to aid in the understanding of the background of the present invention, and is not intended to mean that the present invention falls within the purview of the related art that is already known to those skilled in the art.

SUMMARY

Accordingly, the present disclosure is intended to provide systems and methods for controlling walking of a wearable robot, which applies the force of a virtual spring to provide walking assistive power that is applied as if something were pulling the wearer from the front or pushing the wearer from the back in the walking direction, whereby the wearer of the robot may comfortably walk.

According to one aspect of the present disclosure, there is provided a system for controlling walking of a robot, which includes: a walking mode determination unit configured to determine whether the robot is walking; a virtual spring force calculation unit configured to calculate force of a virtual spring of which one end is connected to the robot and the other end is connected to a target point located in front of the robot based on a walking direction of the robot, when it is determined by the walking mode determination unit that the robot is walking; and a joint driving unit configured to drive joints of the robot using torque that is calculated based on the force of the virtual spring, which is calculated by the virtual spring force calculation unit.

In some implementations, the walking mode determination unit is configured to determine that the robot is walking when the robot is converted from a two foot support state to a one foot support state, and when speed of the robot is equal to or greater than predetermined reference speed.

In some implementations, the virtual spring force calculation unit is configured to calculate the target point based on walking speed of the robot, and predetermined target acceleration or predetermined target speed.

In some implementations, the virtual spring force calculation unit is configured to calculate the target point using previously programmed fuzzy logic, based on walking speed of the robot and predetermined target acceleration or predetermined target speed.

In some implementations, the virtual spring force calculation unit is configured to calculate the target point by the following Equation:

$$x_d = \frac{K_i}{T_i s + 1} \dot{x}_{robot}$$

where $x_d$ denotes the target point, $\dot{x}_{robot}$ denotes walking speed of the robot, and $K_i$ and $T_i$ are optimal control gains, set according to target speed and target acceleration.

In some implementations, the virtual spring force calculation unit is configured to calculate the target point by the following Equation:

$$x_d = a\,\mathrm{sgn}(\dot{x}_{robot}) e^{-k|\dot{x}_{robot}|^\delta} + b\,\mathrm{sgn}(\dot{x}_{robot})$$

where $x_d$ denotes the target point, $\dot{x}_{robot}$ denotes walking speed of the robot, sgn denotes a sign function, and a, b, k, and δ are constants adjusted by target speed or target acceleration.

In some implementations, the virtual spring force calculation unit is configured to calculate the force of the virtual spring by the following Equation:

$$F_{vspring} = -k_{vspring}\Delta x - c_{vspring}\dot{\Delta x}$$

where $\Delta x = x_d - x_c$, $F_{vspring}$ denotes the force of the virtual spring, $x_d$ denotes the target point, $x_c$ denote a current location of the robot, and $k_{vspring}$ and $c_{vspring}$ are predetermined control constants.

According to another aspect of the present disclosure, there is provided a method for controlling walking of a robot, which includes: a walking mode determination operation for determining whether the robot is walking; a target point calculation operation for calculating a target point located in front of the robot based on a walking direction of the robot, depending on walking speed of the robot and predetermined target acceleration or predetermined target speed, when it is determined in the walking mode determination operation that the robot is walking; a virtual spring force calculation operation for calculating force by a virtual spring of which one end is connected to the robot and the other end is connected to the target point; and a joint driving operation for driving joints of the robot using torque calculated based on the force of the virtual spring calculated in the virtual spring force calculation operation.

In implementations of the systems and methods for controlling walking of a wearable robot, described above, the force of a virtual spring connected between the robot and a target point, which is set in the walking direction of the robot, may be applied to the walking of the robot. As a result, the wearer of the robot may feel assistive power applied as if something were pulling or pushing him or her in the walking direction, thus the wearer may comfortably walk.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinafter, systems and methods for controlling walking of a wearable robot will be described in detail with reference to the accompanying drawings.

Figure 1:
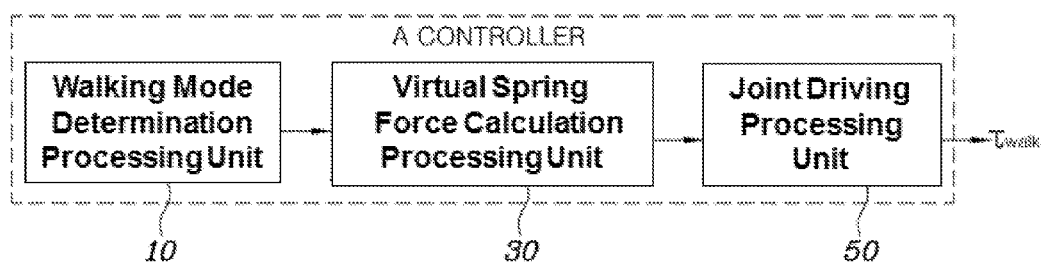
FIG. 1 is a block diagram of a system for controlling walking of a wearable robot.

FIG. 1 is a block diagram of a controller or system for controlling walking of a wearable robot.

As illustrated in FIG. 1, a controller or system for controlling walking of a wearable robot may be configured to include: a walking mode determination processing unit 10 that is configured to determine whether the robot is walking; a virtual spring force calculation processing unit 30 that is configured to calculate the force of a virtual spring of which one end is connected to the robot and the other end is connected to a target point, which is located in front of the robot based on the walking direction, when it is determined by the walking mode determination processing unit 10 that the robot is walking; and a joint driving processing unit 50 that is configured to drive joints of the robot by calculating torque for driving them based on the force of the virtual spring, which is calculated by the virtual spring force calculation processing unit 30.

Figure 2:
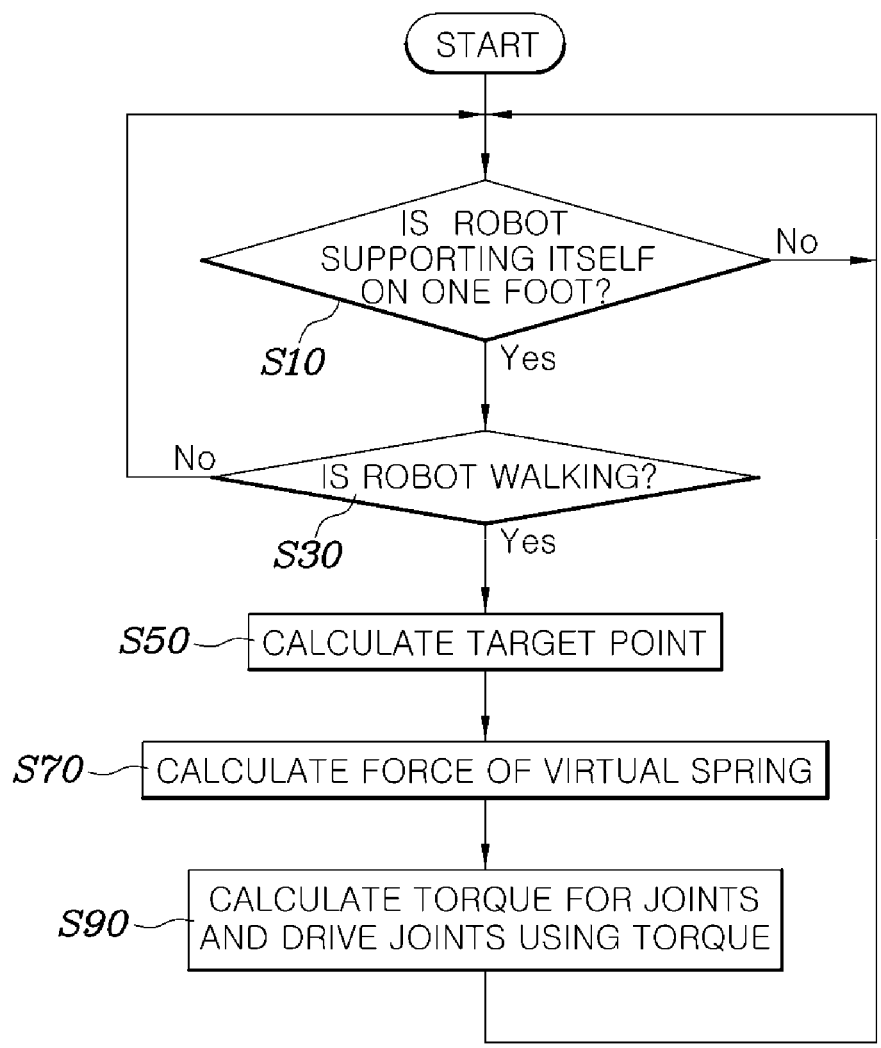
FIG. 2 is a flowchart of a method for controlling walking of a wearable robot.

FIG. 2 is a flowchart of a method for controlling walking of a wearable robot.

Referring to FIG. 2, the method may include: a walking mode determination step (S10, S30) for determining whether a robot is walking; a target point calculation step (S50) for calculating a target point, located in front of the robot based on the walking direction, depending on the walking speed of the robot and predetermined target acceleration or predetermined target speed, when it is determined at the walking mode determination step (S10, S30) that the robot is walking; a virtual spring force calculation step (S70) for calculating the force by a virtual spring of which one end is connected to the robot and the other end is connected to the target point; and a joint driving step (S90) for driving the joints of the robot by calculating torque for driving the joints based on the force of the virtual spring, which is calculated at the virtual spring force calculation step (S70).

Through the above-described configuration, the systems and methods for controlling walking of a wearable robot may apply the force by a virtual spring connected between the robot and a target point, which is set in the walking direction of the robot, to the walking of the robot. Accordingly, the wearer of the robot may feel assistive power as if something were pulling or pushing him or her in the walking direction, whereby the wearer may comfortably walk.

Figure 3:
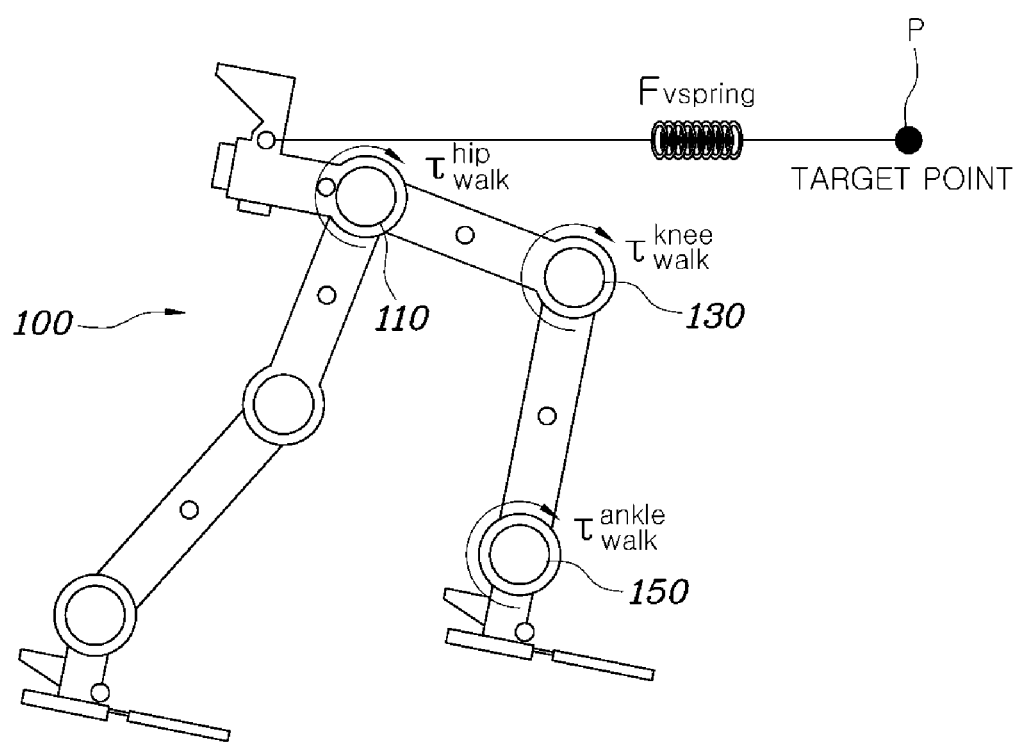
FIG. 3 is a view for explaining the concept of a virtual spring that is applied to a system and method for controlling walking of a wearable robot.
Figure 4:
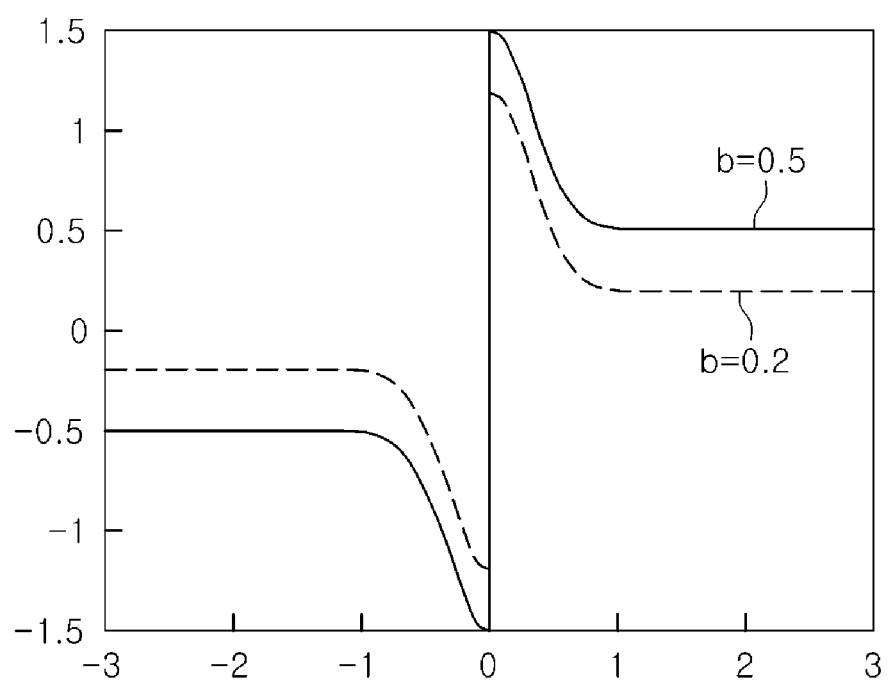
FIG. 4 is a graph for explaining an example for the target point setting method of a system and method for controlling walking of a wearable robot.

FIG. 3 is a view for explaining the concept of a virtual spring applied to the systems and methods for controlling walking of a wearable robot, and FIG. 4 is a graph for explaining an example of the target point setting method of the systems and methods for controlling walking of a wearable robot.

At the walking mode determination step (S10, S30), the walking mode determination unit 10 may determine whether a robot is walking, using various sensors (not illustrated in the drawings) installed in the robot 100. The walking mode determination unit 10 may determine at step S10 whether the robot supports itself on one foot or on both feet using a ground reaction force sensor (not illustrated), which is installed on the soles of the robot 100. The ground reaction force sensor, installed on the soles of the robot, may determine the supporting state by generating different signals respectively for the case in which the sole of the robot is contacted with the ground and for the case in which the sole of the robot is not contacted with the ground.

At the step for determining the supporting state of the robot (S10), when it is determined that the state in which the robot supports itself on both feet is converted into the state in which the robot supports itself on one foot, the walking mode determination unit 10 may determine at step S30 whether the robot has certain speed toward a fixed direction using an acceleration sensor and the like installed in the robot. For example, when the walking mode determination unit 10 determines that the speed in the x-direction at the waist of the robot is greater than predetermined threshold speed after the robot is converted into the one foot support state, it may be determined that the robot has started walking or is walking.

When the walking mode determination unit 10 determines that the robot 100 is converted into the one foot support state and is currently walking, the virtual spring force calculation unit 30 sets a target point P in the walking direction of the robot and calculates the force by a virtual spring of which one end is connected to the robot and the other end is connected to the target point P at step S70.

The target point P may be a certain point located in front of the robot 100 based on the walking direction of the robot. Assuming that there is a virtual spring between the robot (for example, from the waist of the robot) and the target point, when the force by the virtual spring that pulls the robot 100 to the direction of the target point P is applied to the walking of the robot, the wearer of the robot may feel the force as if something were pulling him or her from the front or pushing him or her from the back, whereby the wearer may comfortably walk.

At the target point calculation step (S50), the virtual spring force calculation unit 30 may calculate the target point by applying various methods based on the walking speed of the robot and predetermined target acceleration or predetermined target speed.

For example, at the target point calculation step (S50), the virtual spring force calculation unit 30 may obtain the target point by applying previously programmed fuzzy logic. The current walking speed of the robot and the predetermined target acceleration or target speed become the inputs of the fuzzy logic. In order to determine the location of the target point, which corresponds to the output of the fuzzy logic, the fuzzy logic may apply previously specified rules and preset conditions to the inputs.

As another example, the virtual spring force calculation unit 30 may determine the target point by applying conditional statements and equations.

An example for applying the conditional statements and the equations is shown as the following Equation (1):

$$x_d = \frac{K_i}{T_i s + 1} \dot{x}_{robot} \quad (1)$$

where $x_d$ denotes the target point, $\dot{x}_{robot}$ denotes the current walking speed of the robot 100, and $K_i$ and $T_i$ are optimal control gains, which are set according to the predetermined target speed and target acceleration of the robot.

As shown in Equation (1), the virtual spring force calculation unit 30 may obtain the target point by applying the optimal control method.

Another example for applying the conditional statements and equations is shown as the following Equation (2):

$$x_d = a\,\mathrm{sgn}(\dot{x}_{robot}) e^{-k|x_{robot}|^\delta} + b\,\mathrm{sgn}(\dot{x}_{robot}) \quad (2)$$

where $x_d$ denotes the target point, $\dot{x}_{robot}$ denotes the current walking speed of the robot 100, sgn denotes a sign function, and a, b, k, and δ are constants adjusted by the target speed or target acceleration.

FIG. 4 is a graph illustrating an example of the target point determined by applying the above Equation (2). According to Equation (2) and FIG. 4, at the target point calculation step (S50), the virtual spring force calculation unit 30 applies great force when walking is started, and sets a fixed target location when the walking speed is equal to or greater than certain speed. By adjusting the value of k, the virtual spring force calculation unit 30 may determine the target point according to the desired target acceleration. For example, as the target acceleration is higher, the value of k may be higher (k>0). Also, the virtual spring force calculation unit 30 may determine the target point according to the target speed by adjusting the value of b. For example, as the target speed is higher, the value of b may be higher (b>=0). Specifically, FIG. 4 illustrates the comparison between the case in which the value of b is 0.2 and the case in which the value of b is 0.5, under the condition where a=1, k=0.5 and δ=2.

Besides, the virtual spring force calculation unit 30 may obtain the target point using a reference table, which previously sets the relation among the location of the target point, the walking speed of the robot, and the predetermined target acceleration or target speed, at the target point calculation step (S50).

After the location of the target point is calculated at the target point calculation step (S50), the virtual spring force calculation unit 30 may perform the virtual spring force calculation step (S70). At step S70, the force of the virtual spring may be calculated as the following Equation (3):

$$F_{vspring} = -k_{vspring} \Delta x - c_{vspring} \Delta \dot{x} \quad (3)$$

where $\Delta x = x_d - x_c$, $F_{vspring}$ denotes the force of the virtual spring, $k_{vspring}$ and $c_{vspring}$ are predetermined control constants, $x_d$ denotes the target point, and $x_c$ denote the current location of the robot 100.

Subsequently, at the joint driving step (S90), the joint driving unit 50 may convert the force of the virtual spring, which was calculated at the virtual spring calculation step (S70), into target torque to be applied to the respective joints 110, 130, and 150 of the robot. The conversion into the target torque, performed at the joint driving step (S90) may be calculated by the following Equation (4):

$$\tau_{walk} = \begin{cases} J^T F_{vspring} & SSP \\ 0 & \text{otherwise} \end{cases} \quad (4)$$

where $J^T$ denotes Jacobian transpose, and SSP means the walking when the robot supports itself on one foot. In other words, the torque to which the force of the virtual spring is applied may be applied when the robot is walking by being converted from the two foot support state to the one foot support state.

At the joint driving step (S90), the joint driving unit 50 drives the joints 110, 130, and 150 of the robot 100 using the torque calculated by Equation (4), whereby the force by the virtual spring may be applied to the driving of the joints.

As described above, the systems and methods for controlling walking of an wearable robot applies the force of a virtual spring to driving of the joints of a robot to help stability and gait in the walking direction (pitch direction) when the walking by the robot is converted from a two foot support state to a one foot support state, whereby the load felt by the wearer of the robot may be reduced and the robot may help the wearer to comfortably walk.

Although a preferred forms of the present invention has been described for illustrative purposes, those skilled in the art will appreciate that various modifications, additions and substitutions are possible, without departing from the scope and spirit of the invention as disclosed in the accompanying claims.

What is claimed is:

1. A controller for walking of a robot, comprising:
   a walking mode determination processing unit configured to determine whether the robot is walking;
   a virtual spring force calculation processing unit configured to calculate force of a virtual spring of which one end is connected to the robot and the other end is connected to a target point located in front of the robot based on a walking direction of the robot, when it is determined by the walking mode determination processing unit that the robot is walking; and
   a joint driving processing unit configured to drive joints of the robot using torque calculated based on the force of the virtual spring, which is calculated by the virtual spring force calculation processing unit;
   wherein the virtual spring force calculation processing unit is configured to calculate the target point based on walking speed of the robot, and predetermined target acceleration or predetermined target speed;
   wherein the virtual spring force calculation processing unit configured to apply great force when walking is started, and set a fixed target location when the walking speed is equal to or greater than a certain speed.

2. The controller of claim 1, wherein the walking mode determination processing unit is configured to determine that the robot is walking when the robot is converted from a two foot support state to a one foot support state, and when speed of the robot is equal to or greater than predetermined reference speed.

3. The controller of claim 1, wherein the virtual spring force calculation processing unit is configured to calculate the target point using previously programmed fuzzy logic, based on walking speed of the robot and predetermined target acceleration or predetermined target speed.

4. The controller of claim 1, wherein the virtual spring force calculation processing unit is configured to calculate the target point by the following Equation:

$$x_d = \frac{K_i}{T_i s + 1} \dot{x}_{robot}$$

where $x_d$ denotes the target point, $\dot{x}_{robot}$ denotes walking speed of the robot, and $K_i$ and $T_i$ are optimal control gains, set according to target speed and target acceleration.

5. The controller of claim 1, wherein the virtual spring force calculation processing unit is configured to calculate the target point by the following Equation:

$$x_d = a\,\mathrm{sgn}(\dot{x}_{robot})e^{-k|\dot{x}_{robot}|^\delta} + b\,\mathrm{sgn}(\dot{x}_{robot})$$

where $x_d$ denotes the target point, $\dot{x}_{robot}$ denotes walking speed of the robot, sgn denotes a sign function, and a, b, k, and δ are constants adjusted by target speed or target acceleration.

6. The controller of claim 1, wherein the virtual spring force calculation processing unit is configured to calculate the force of the virtual spring by the following Equation:

$$F_{vspring} = -k_{vspring}\Delta x - c_{vspring}\dot{\Delta x}$$

where $\Delta x = x_d - x_c$, $F_{vspring}$ denotes the force of the virtual spring, $x_d$ denotes the target point, $x_c$ denote a current location of the robot, and $k_{vspring}$ and $c_{vspring}$ are predetermined control constants.

7. A method for controlling walking of a robot, comprising:
   a walking mode determination operation for determining whether the robot is walking;
   a target point calculation operation for calculating a target point located in front of the robot based on a walking direction of the robot, depending on walking speed of the robot and predetermined target acceleration or predetermined target speed, when it is determined in the walking mode determination operation that the robot is walking;
   a virtual spring force calculation operation for calculating force by a virtual spring of which one end is connected to the robot and the other end is connected to the target point; and
   a joint driving operation for driving joints of the robot using torque calculated based on the force of the virtual spring calculated in the virtual spring force calculation operation;
   wherein the virtual spring force calculation operation for applying great force when walking is started, and setting a fixed target location when the walking speed is equal to or greater than a certain speed.

8. The method of claim 7, wherein the walking mode determination operation comprises:
   determining whether the robot is converted from a two foot support state to a one foot support state; and
   determining that the robot is walking if speed of the robot when the robot is converted into the one foot support state is equal to or greater than predetermined reference speed.

9. The method of claim 7, wherein the target point calculation operation is configured to calculate the target point using previously programmed fuzzy logic, based on the walking speed of the robot and the predetermined target acceleration or predetermined target speed.

10. The method of claim 7, wherein the target point calculation operation is configured to calculate the target point by the following Equation:

$$x_d = \frac{K_i}{T_i s + 1} \dot{x}_{robot}$$

where $x_d$ denotes the target point, $\dot{x}_{robot}$ denotes the walking speed of the robot, and $K_i$ and $T_i$ are optimal control gains, set according to the target speed and target acceleration.

11. The method of claim 7, wherein the target point calculation operation is configured to calculate the target point by the following Equation:

$$x_d = a\,\mathrm{sgn}(\dot{x}_{robot})e^{-k|\dot{x}_{robot}|^\delta} + b\,\mathrm{sgn}(\dot{x}_{robot})$$

where $x_d$ denotes the target point, $\dot{x}_{robot}$ denotes the walking speed of the robot, sgn denotes a sign function, and a, b, k, and δ are constants adjusted by the target speed or the target acceleration.

12. The method of claim 7, wherein the target point calculation operation is configured to calculate the force of the virtual spring by the following Equation:

$$F_{vspring} = -k_{vspring}\Delta x - c_{vspring}\dot{\Delta x}$$

where $\Delta x = x_d - x_c$, $F_{vspring}$ denotes the force of the virtual spring, $x_d$ denotes the target point, $x_c$ denote a current location of the robot, and $k_{vspring}$ and $c_{vspring}$ are predetermined control constants.

* * * * *